(12) United States Patent
Kennedy

(10) Patent No.: US 8,512,689 B2
(45) Date of Patent: Aug. 20, 2013

(54) ANIMAL SCENT PRESERVATION

(76) Inventor: Mickey McArthur Kennedy, Medina, OH (US)

( * ) Notice: Subject to any disclaimer, the term of this patent is extended or adjusted under 35 U.S.C. 154(b) by 0 days.

(21) Appl. No.: 13/065,452

(22) Filed: Mar. 23, 2011

(65) Prior Publication Data

US 2012/0244109 A1    Sep. 27, 2012

(51) Int. Cl.
*A01N 63/02* (2006.01)
*A01P 19/00* (2006.01)
*B65B 1/04* (2006.01)

(52) U.S. Cl.
USPC ............ 424/84; 43/1; 422/1; 53/473; 53/467; 241/38

(58) Field of Classification Search
None
See application file for complete search history.

(56) References Cited

U.S. PATENT DOCUMENTS

| 4,883,021 | A * | 11/1989 | Ducharme et al. | 119/171 |
| 2005/0246938 | A1* | 11/2005 | Windus | 43/1 |
| 2006/0263326 | A1* | 11/2006 | Weiser | 424/74 |

OTHER PUBLICATIONS

Yves Mayeresse, Vinciane de Cupere, Romain Veillon, and Joseph Brendle. Considerations for Transferring a Bulk Freeze-Drying Process from a Glass Container to a Tray. Pharmaceutical Engineering, Mar./Apr. 2009, pp. 1-8.*
Product data sheet for Gore Lyoguard Freeze Drying Tray, downloaded Apr. 25, 2012 from the internet site: http://www.gore.com/en_xx/products/pharmaceutical/lyophilization/technical_specifications_lyoguard_freeze_drying_tray.html.*

* cited by examiner

*Primary Examiner* — Frederick Krass
*Assistant Examiner* — Michael P Cohen

(57) ABSTRACT

The disclosed subject matter relates to a mixture that can facilitate preservation of animal scent, such as, e.g., doe pee; as well as to an apparatus and method for creating the mixture.

9 Claims, 3 Drawing Sheets

ANIMAL SCENT PRESERVATION

TECHNICAL FIELD

The present application relates generally to preservation and or long-term storage of animal scent such as, for example, deer or doe pee, without significant loss of efficacy.

BACKGROUND

In the domain of game hunting as well as other consumer and commercial uses, animal scents, such as urine, are commonly employed. Unfortunately, animal scent in its liquid form has a reduced shelf-life, and will evaporate quickly or otherwise lose its effectiveness. Thus, what is needed is a way of preserving animal scents while retaining various desired characteristics of the animal scent.

DETAILED DESCRIPTION

Overview

Figure 1:
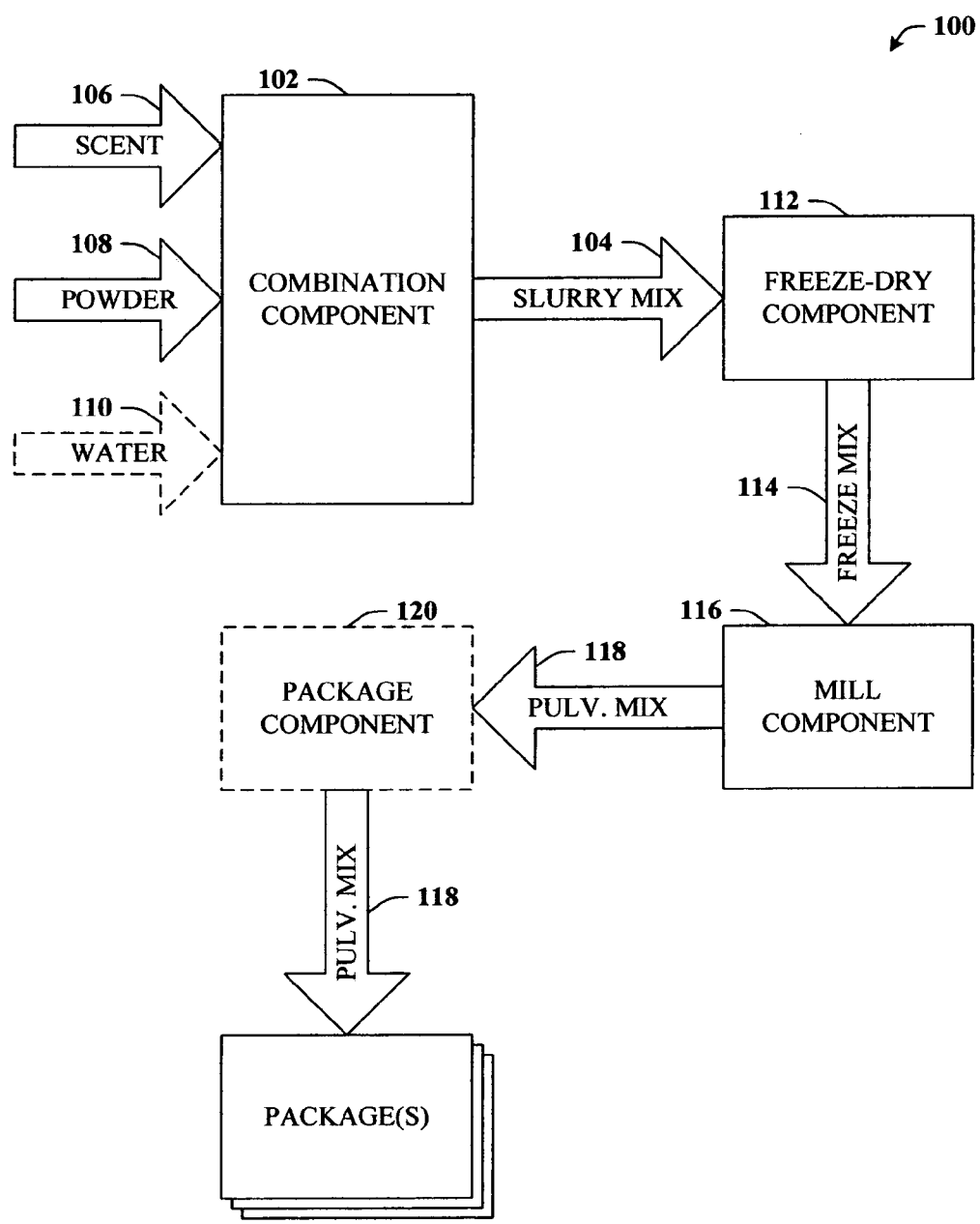
FIG. 1 is an example apparatus that can facilitate preservation of animal scent.

The scent from doe pee or any other scent bearing liquid can be preserved by using the following process if followed properly and can be rejuvenated by re-introducing warm or cold water.

First step: Using tested amounts of doe or any other pee or scents from known species of animals and a ratio of liquid to powder, simply mix thoroughly into a slurry mixture consistent to pancake batter.

Second step: Pour into a flat tray approximately ¾ to 1 inch thick and place into a freeze dry chamber. Start freeze dry process and remove from chamber when all moisture content is removed from mixture.

Third step: Pulverize mixture into a powder and package in a bag similar to a tee bag and place in a small baggie with string and label.

Fourth step: When ready to use simply place bag in cold or warm water. This will release the scent stored in the powder and will remain fresh for approximately two weeks.

Packaging does not have to be in a tea bag type container and can be freely mixed in measured amount of water. This processed powder can also be dusted directly upon the ground for scent release.

An example mixture can be equal weights of two parts powdered oats, two parts powdered soy bean and 3 parts urine with two parts water.

The pulverized powder is not limited to the aforementioned process and can be any powder derived from various products which can be soluble in water or any other liquid.

Animal Scent Preservation

The disclosed subject matter is now described with reference to the drawings, wherein like reference numerals are used to refer to like elements throughout. In the following description, for purposes of explanation, numerous specific details are set forth in order to provide a thorough understanding of the disclosed subject matter. It may be evident, however, that the disclosed subject matter may be practiced without these specific details. In other instances, well-known structures and devices are shown in block diagram form in order to facilitate describing the disclosed subject matter.

As used herein, the word "exemplary" is used to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring now to the drawing, with reference initially to FIG. 1, apparatus 100 that can facilitate preservation of animal scent is depicted. In particular, apparatus 100 can include combination component 102 that can be configured to create slurry mixture 104 associated with preservation of animal scent 106. Slurry mixture 104 can be characterized by a mixture of animal scent 106 and preservation powder 108, as well as, optionally, water 110, which is further detailed infra.

In one or more aspect, animal scent 106 can be comprised of animal urine or a derivative thereof. For example, animal scent 106 can be deer or doe pee. Furthermore, in one or more aspect preservation powder 108 can be characterized by absorption or retention of animal scent 106 or pheromones included in animal scent 106. By way of example and not necessarily limitation, preservation powder 108 can be or can include powdered oats. As another example, preservation powder 108 can be or can include powdered soy beans. As yet another example, preservation powder 108 can be or can include a combination of oats, soy beans, or substantially any other suitable powder or material.

In one particular embodiment, slurry mixture 104 can be comprised of approximately three parts animal scent 106, two parts powdered oats, and two parts powdered soy beans, wherein a ratio of combination can be based upon weight. Moreover, as introduced above, combination component 102 can be further configured to adjust a consistency of slurry mixture 104 based upon an addition of water 110. Thus, in one particular embodiment, slurry mixture 104 can be comprised of approximately three parts animal scent 106, two parts powdered oats, two parts powdered soy beans, and two parts water 110, again with ingredient parts based upon weight.

While water 110 is not strictly necessary, by adding water 110 to slurry mixture 104, a desired consistency can be obtained that can be more conducive to mixing slurry mixture 104. It has been found that a consistency of slurry mixture 104 that is similar to that of pancake batter can produce excellent results. Hence, water 110 can be added to achieve that or another desired consistency.

In addition, system 100 can also include freeze-dry component 112, which can receive slurry mixture 104. Freeze-dry component 112 can be configured to create a freeze-dried mixture 114 characterized by freeze-drying slurry mixture 104. In one or more aspect, the efficacy of the freeze-drying process can be enhanced by increasing the available surface area of the slurry mixture. Thus, slurry mixture 104 can be poured or spread in thin layers, for example less than two inches in height, or, e.g., between three-quarters of an inch and one inch in height.

Furthermore, system 100 can further include mill component 116 that can be configured to create pulverized mixture 118. Pulverized mixture 118 can be characterized pulverizing freeze-dried mixture 114, either or both of which represent a means of preserving animal scent 106 in a non-volatile state. Hence, pulverized mixture 118 (or freeze-dried mixture 114) can store desired properties of animal scent 106, yet is not prone to evaporation or the common rapid loss of efficacy. In practice, pulverized mixture 118 (or freeze-dried mixture 114) can be utilized in powdered form (e.g., sprinkling the powder at a desired location) or can be reconstituted as a liquid, e.g., by adding an amount of water or another suitable liquid.

Regardless, system 100 can optionally include package component 120 that can be configured to package an amount of pulverized mixture 118 (or freeze-dried mixture 114). In one or more aspect, package component 120 can be configured to add the amount of pulverized mixture 118 to a package configured for steeping, such as, for example, a package similar to a tea bag. Additionally or alternatively, package component 120 can be configured to add the amount of pulverized mixture 118 to a hermetically sealed back and/or a substantially air-tight package.

Figure 2:
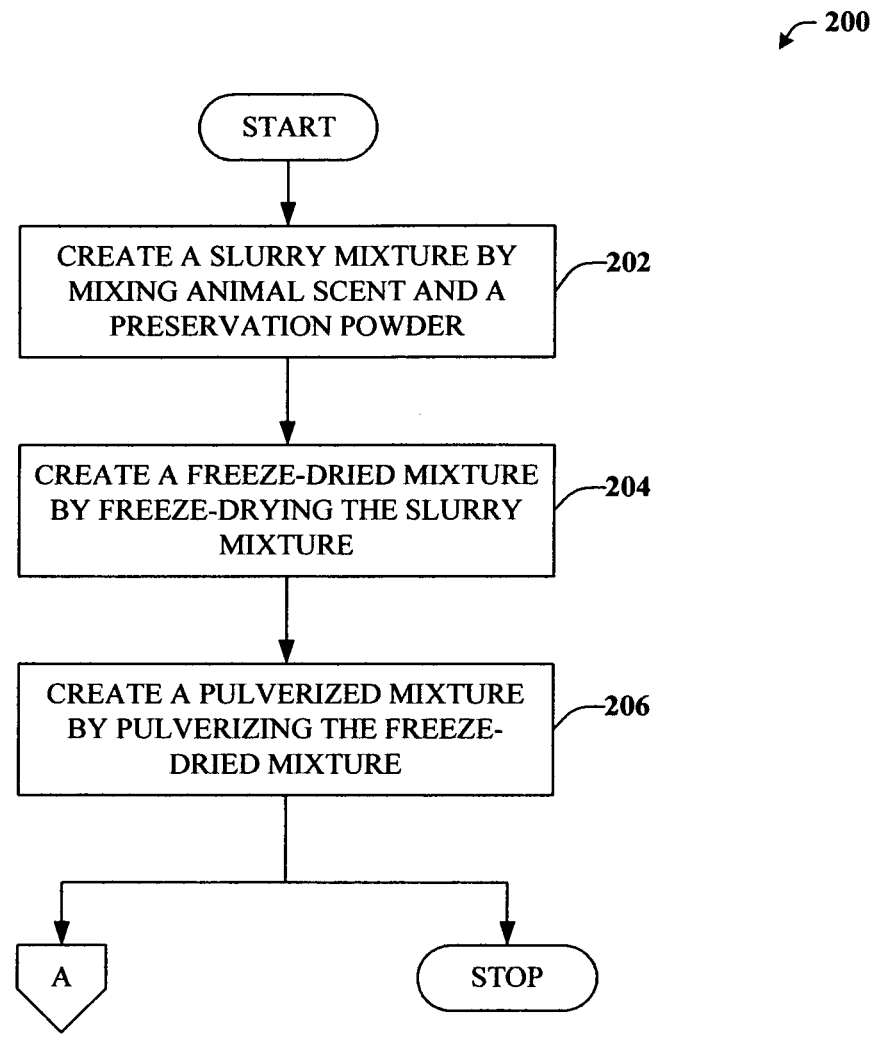
FIG. 2 depicts an exemplary flow chart of procedures defining a method for preserving animal scent.
Figure 3:
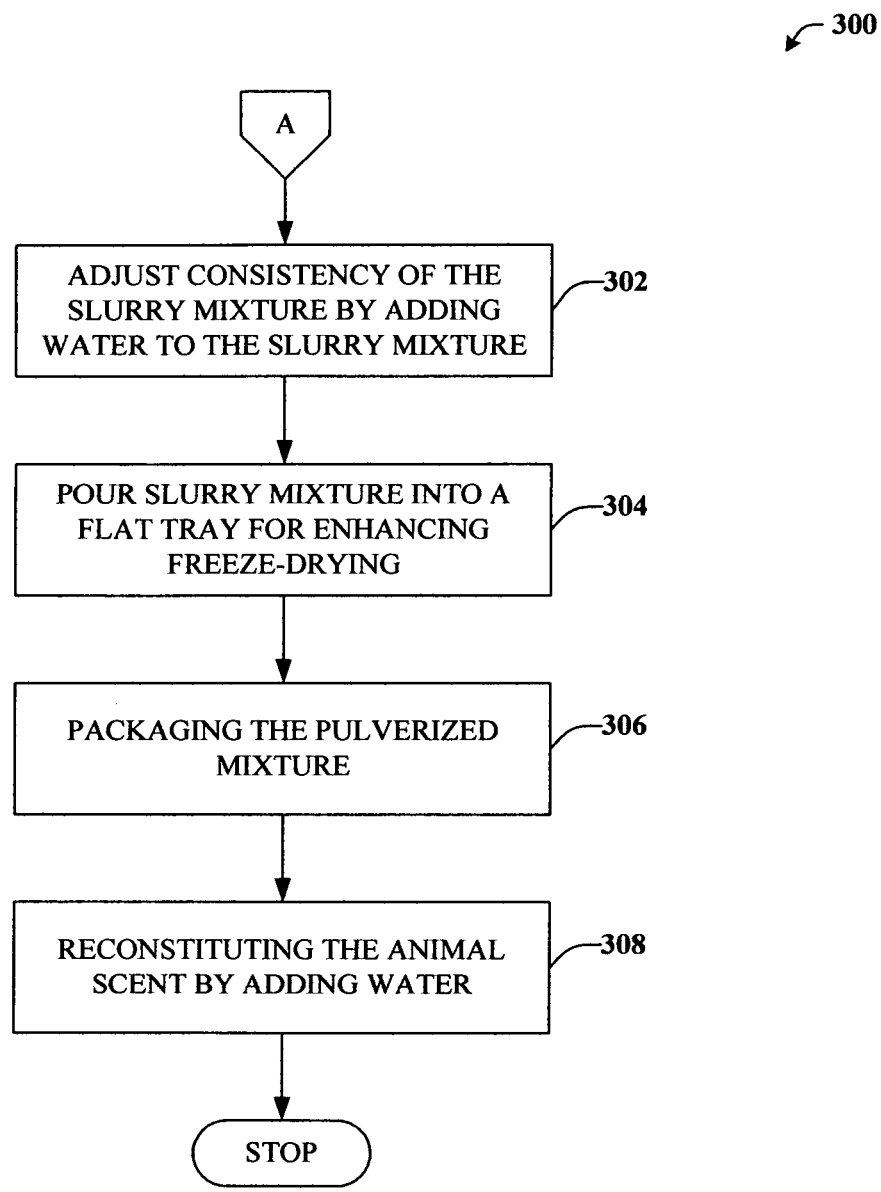
FIG. 3 illustrates an exemplary flow chart of procedures defining a method for providing additional features or aspects in connection with preserving animal scent.

FIGS. 2-3 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts may occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the disclosed subject matter. Additionally, it should be further appreciated that the methodologies disclosed hereinafter and throughout this specification are capable of being stored on an article of manufacture to facilitate transporting and transferring such methodologies to computers.

Turning now to FIG. 2, example method 200 for preserving animal scent is provided. In general, at reference numeral 202, a slurry mixture can be created, wherein the slurry mixture can be characterized by mixing animal scent (e.g., urine) and a preservation powder (e.g., powders able to absorb or retain the animal scent or pheromones thereof, such powdered oats, powdered soy beans, or the like).

Next to be described, at reference numeral 204, a freeze-dried mixture can be created, wherein the freeze-dried mixture can be characterized by freeze-drying the slurry mixture created at reference numeral 202. Accordingly, at reference numeral 206, a pulverized mixture can be created. The pulverized mixture can be characterized by pulverizing the freeze-dried mixture created at reference numeral 204.

Referring now to FIG. 3, method 300 for providing additional features or aspects in connection with preserving animal scent is illustrated. For example, at reference numeral 302, a consistency of the slurry mixture created at reference numeral 202 of FIG. 2 can be adjusted. Any such adjustment to the consistency can be characterized by adding water to the slurry mixture.

Regardless, at reference numeral 304, the slurry mixture can be poured into or spread upon a flat tray, e.g., for enhancing the efficacy of the freeze-drying process detailed in connection with reference numeral 204. For example, the tray can be configured to support contents of two inches or less.

Advantageously, at reference numeral 306, the pulverized mixture can be packaged. For example, the pulverized mixture can be packaged into packages configured for steeping, similar to a tea bag. Additionally or alternatively, the pulverized mixture can be hermetically sealed.

Moreover, in one or more aspect, the animal scent can be reconstituted in liquid form, e.g., by adding water or another suitable liquid to the pulverized mixture (reference numeral 308).

What has been described above includes examples of the various embodiments. It is, of course, not possible to describe every conceivable combination of components or methodologies for purposes of describing the embodiments, but one of ordinary skill in the art may recognize that many further combinations and permutations are possible. Accordingly, the detailed description is intended to embrace all such alterations, modifications, and variations that fall within the spirit and scope of the appended claims.

In particular and in regard to the various functions performed by the above described components, devices, apparatuses, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the embodiments. In this regard, it will also be recognized that the embodiments includes a system as well as a computer-readable medium having computer-executable instructions for performing the acts and/or events of the various methods.

In addition, while a particular feature may have been disclosed with respect to only one of several implementations, such feature may be combined with one or more other features of the other implementations as may be desired and advantageous for any given or particular application. Furthermore, to the extent that the terms "includes" and "including" and variants thereof are used in either the detailed description or the claims, these terms are intended to be inclusive in a manner similar to the term "comprising."

What is claimed is:

1. A method for preserving animal scent, comprising:
creating a slurry mixture by mixing animal scent and a preservation powder;
creating a freeze-dried mixture by freeze-drying the slurry mixture; and
creating a pulverized mixture by pulverizing the freeze-dried mixture, wherein the animal scent is urine and the preservation powder consists of at least one of powdered oats or powdered soybeans.

2. The method of claim 1, further comprising adjusting a consistency of the slurry mixture characterized by adding water to the slurry mixture.

3. The method of claim 1, further comprising pouring the slurry mixture into a flat tray, approximately one or two inches in height or less for enhancing a freeze-drying process.

4. The method of claim 1, further comprising packaging the pulverized mixture.

5. The method of claim 4, wherein the packaging the pulverized mixture comprises packaging the pulverized mixture in containers adapted for steeping.

6. The method of claim 4, wherein the packaging the pulverized mixture comprises hermetically sealing the pulverized mixture.

7. The method of claim 1, wherein the preservation powder comprises a combination of powdered oats and powdered soy beans.

8. A method for preserving animal scent, comprising:
creating a slurry mixture by mixing animal scent and a preservation powder;
creating a freeze dried mixture by freeze-drying the slurry mixture; and
creating a pulverized mixture by pulverizing the freeze-dried mixture;
wherein the animal scent is urine and the preservation powder comprises approximately two parts powdered oats, two parts powdered soy beans, three parts animal scent, and two parts water.

9. The method of claim 1, further comprising reconstituting the animal scent characterized by adding water to the pulverized mixture.

\* \* \* \* \*